(12) United States Patent
Cerefice et al.

(10) Patent No.: US 6,696,604 B2
(45) Date of Patent: Feb. 24, 2004

(54) ADDITION OF MINERAL ACIDS OR SALTS THEREOF TO A TMA PRODUCTION PROCESS

(75) Inventors: Steven A. Cerefice, Naperville, IL (US); Wayne P. Schammel, Naperville, IL (US); David A. Young, Hartselle, AL (US)

(73) Assignee: BP Corporation North America Inc., Warrenville, IL (US)

( * ) Notice: Subject to any disclaimer, the term of this patent is extended or adjusted under 35 U.S.C. 154(b) by 121 days.

(21) Appl. No.: 10/036,551

(22) Filed: Jan. 3, 2002

(65) Prior Publication Data

US 2002/0143192 A1 Oct. 3, 2002

Related U.S. Application Data

(60) Provisional application No. 60/262,941, filed on Jan. 19, 2001.

(51) Int. Cl.$^7$ .................................................. C07C 65/00
(52) U.S. Cl. ...................... 562/888; 562/405; 562/407; 562/409
(58) Field of Search ................................. 562/887, 888, 562/898, 405, 407, 409, 412

(56) References Cited

U.S. PATENT DOCUMENTS

| | | | |
|---|---|---|---|
| 3,732,257 A | 5/1973 | Knobloch et al. | 260/346.4 |
| 3,798,238 A | 3/1974 | Meyer | 260/346.4 |
| 4,788,296 A | 11/1988 | Robbins et al. | 549/245 |
| 4,948,921 A | 8/1990 | Green et al. | 562/413 |

FOREIGN PATENT DOCUMENTS

EP 896960 2/1999

*Primary Examiner*—Johann Richter
*Assistant Examiner*—Karl Puttlitz
(74) *Attorney, Agent, or Firm*—Mary Jo Kanady

(57) ABSTRACT

This invention is related to the production of trimellitic anhydride (TMA). More specifically, the invention is related to the addition of a mineral acid or salt thereof in the production process of trimellitic anhydride to reduce the viscosity of the bottoms fraction when TMA is purified by distillation and thus to prevent fouling/plugging. This permits the use of lower levels of TMA in the bottoms fraction and increases TMA recovery.

10 Claims, 1 Drawing Sheet

ADDITION OF MINERAL ACIDS OR SALTS THEREOF TO A TMA PRODUCTION PROCESS

This application claims the benefit of U.S. Provisional Application No. 60/262,941 filed Jan. 19, 2001, which is incorporated herein by reference in its entirety.

FIELD OF THE INVENTION

This invention is generally related to the production of 1,3-dihydro-1,3-dioxo-5-isobenzofuran carboxylic acid more commonly known as trimellitic anhydride (TMA). More specifically, the invention is related to the addition of a mineral acid or salt thereof in the production process of trimellitic anhydride.

BACKGROUND OF THE INVENTION

Trimellitic anhydride (TMA) is a commercial chemical intermediate useful in various areas including plasticizers and specialty coatings.

TMA is commonly produced by the oxidation of pseudocumene (1,2,4-trimethylbenzene) to trimellitic acid (1,2,4-benezenetricarboxylic acid) followed by dehydration to form the anhydride. The oxidation of pseudocumene to trimellitic acid is preformed using a metal catalyst system.

After oxidation of pseudocumene and dehydration to form the anhydride, the resulting crude TMA is fed into a fractionation column for purification. In this distillation step, the crude TMA is separated into a relatively low boiling point fraction and a less volatile bottoms fraction. The low boiling point fraction is recovered from the top of the column as purified TMA while the bottoms fraction falls to the bottom of the column where it is recycled back to the column through a reboiler. The bottoms fraction contains TMA and various impurities including: 1) multivalent metals from the catalyst system used for oxidation of pseudocumene and 2) aromatic polycarboxylic acids byproducts. Since these impurities are concentrated in the bottoms fraction as it is recycled, some amount of the bottoms portion is periodically or continuously removed though a bottoms purge stream and combined with other waste streams to be incinerated.

A problem encountered during the distillation step is that the viscosity of the bottoms fraction increases as the bottoms are continuously recycled and the more volatile TMA is removed. If unchecked, the viscosity reaches a point where fouling or plugging of the fractionation column occurs. More commonly a high viscosity in the bottoms leads to fouling or plugging of the bottoms purge stream and/or the reboiler. Such fouling or plugging means a significant economic loss due to: 1) the time and expense required to clean and return the column to an operable state and 2) the loss of production capacity. One solution to the problem has been to maintain high levels of TMA in the bottoms fraction in order to reduce viscosity. Unfortunately, maintaining high levels of TMA in the bottoms fraction results in a yield loss, i.e. lower recovery of TMA from the top of the column since high levels of TMA exit the fractionation column though the bottoms purge stream instead. Accordingly, it would be desirable to discover a way of reducing the viscosity of the recycled bottoms fraction contained in a fractionation column for TMA, thereby reducing the amount of TMA required in the bottoms to prevent fouling/plugging and ultimately increasing the amount of TMA recovered from the top of the column.

SUMMARY OF THE INVENTION

The present invention solves the problem of increasing the level of TMA recovery in a fractionation column while also preventing fouling/plugging of the column resulting from the high viscosity of the bottoms fraction. The present invention solves this problem by the addition of a mineral acid or salt thereof to the process. It has been surprisingly discovered that the addition of a mineral acid or salt thereof reduces the viscosity of the bottoms and permits the use of lower levels of TMA in the bottoms fraction necessary to prevent fouling/plugging.

The present invention is a method for making trimellitic anhydride comprising:

a) oxidizing pseudocumene in the presence of a solvent and a catalyst comprising multivalent metals to produce trimellitic acid;

b) crystallizing and filtering said trimellitic acid to produce a crude trimellitic acid cake having impurities comprising said multivalent metals;

c) dehydrating said crude trimellitic cake to form crude trimellitic anhydride; and d) distilling said crude trimellitic anhydride in a fractionation column;

wherein a viscosity modifier is added after step a) but before step d) so that said viscosity modifier is present in said bottoms fraction.

While it is not intended that this invention be bound or limited by any particular theory, it is believed that the viscosity of the bottoms fraction is related to the presence and interaction of impurities in the crude TMA. Impurities in the bottoms fraction comprise multivalent metals that are present from the metal catalyst system and organic by-products from the oxidation of pseudocumene to trimellitic acid. Multivalent metals that are present as impurities may include cobalt(II), cobalt(III), cerium(III), cerium(IV), manganese(II), manganese(III), zirconium(IV). Organic impurities may also include various aromatic polycarboxylic acids and anhydrides thereof. Examples of these aromatic acids are trimellitic acid, 1,2,3,4-tetracarboxylic acid, 1,2,4,5-tetracarboxylic acid and 1,2,3,5-tetracarboxylic acid.

It is theorized that the multivalent metals and the acids and anhydrides thereof form polymeric complexes which increase the viscosity of the bottoms fraction. It is believed the formation of these polymeric complexes results from the ability of the multivalent metals to form complex salts with the aromatic acids and an hydrides thereof. Since aromatic polycarboxylic acids and anhydrides thereof provide multiple sites for the formation of salts, it is believed that polymer structures having repeating unit represented by -(A-B)$_n$- are formed, wherein A-B is a salt formed by a multivalent metal(A) and a acid(B). It is further hypothesized that high molecular weight and highly branched polymers are formed which result in a higher viscosity of the bottoms fraction.

It is believed that a mineral acid or salt thereof interferes with the formation of such polymers by forming lower molecular weight and/or less branched salts of the mineral acid with the multivalent metals. Accordingly, it is thought that the addition of a mineral acid reduces viscosity of the bottoms fraction by hindering or preventing the multivalent metals and aromatic acids from forming polymeric complexes.

DETAILED DESCRIPTION OF THE INVENTION

Production of TMA

Figure 1:
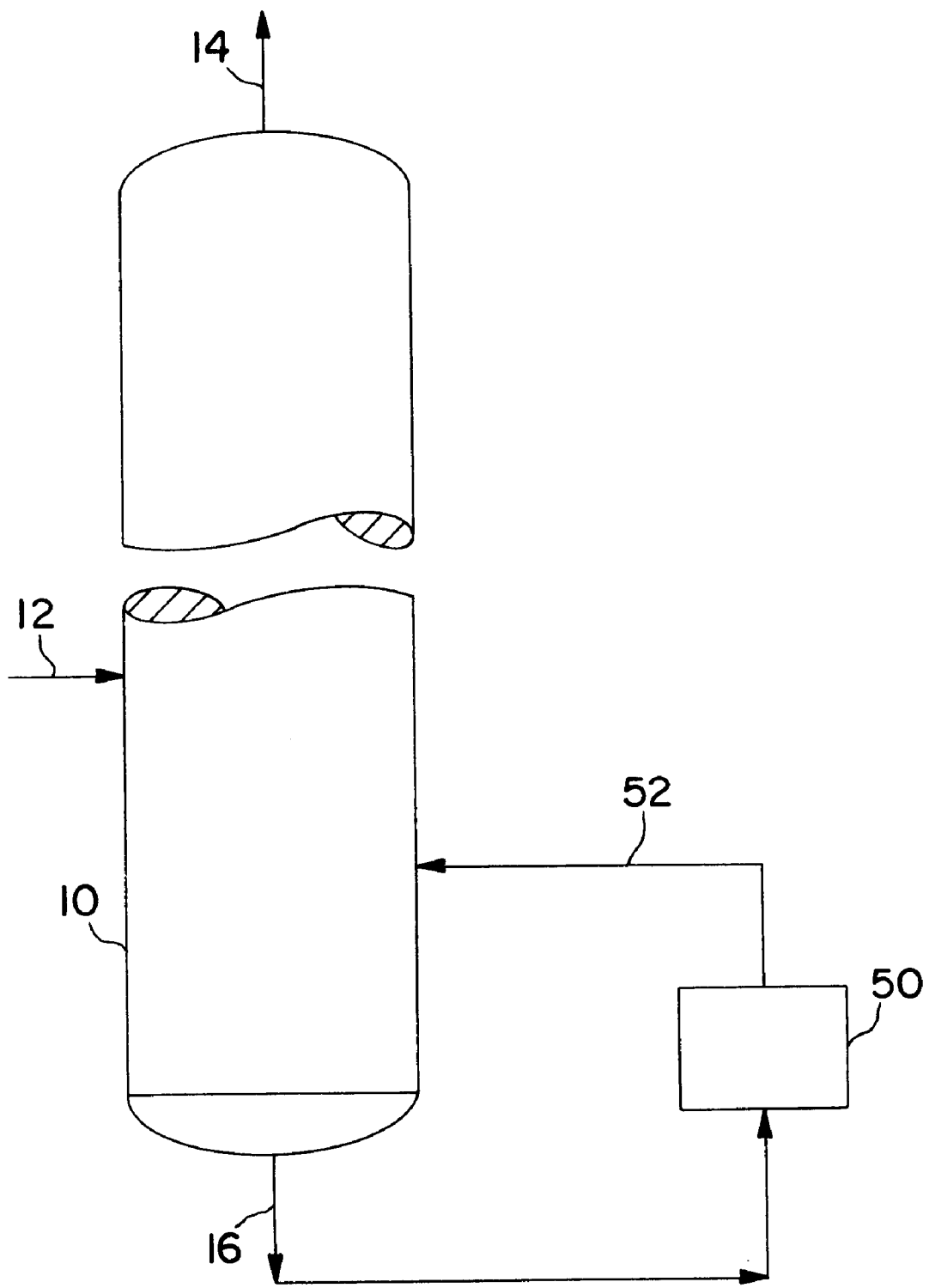
FIG. 1 is a representation of a typical fractionation column.

Although not limited by any particular process for producing TMA, the present invention may be better understood though the following description of a typical TMA production process. The production of TMA may be described as comprising four steps: 1) oxidation, 2) crystallization and filtration, 3) dehydration, and 4) distillation.

In the first step, pseudocumene in the presence of acetic acid solvent and a catalyst solution, is oxidized to trimellitic acid in oxidation reactors operated under pressure to maintain reaction temperatures. The catalyst solution typically comprises cobalt acetate, cerium acetate, manganese acetate, zirconium acetate, and hydrogen bromine. Compressed air is metered into the reactors and air oxidation of the pseudocumene to trimellitic acid occurs. The exothermic heat of reaction is removed by condensing the boiling solvent and returning it as subcooled condensate directly to the reactor.

In the second step, crystallization and filtration, total reactor effluent is crystallized in a depressuring-cooling cycle, with solvent vapor removal, to separate trimellitic acid as a crystalline solid from the soluble oxidation by-products, intermediates, and multivalent metals. The crude trimellitic acid crystals are separated from the mother liquor by vacuum filtration and washed with fresh acetic acid to produce a crude trimellitic acid wet cake.

In the third step, dehydration, the trimellitic acid wet cake is dropped into a molten pool of trimellitic anhydride where solvent flashes off and the crystals dehydrate to form crude TMA.

In the forth step, distillation, the crude TMA is fed into a fractionation column. A typical fractionation column for use in the production of TMA is depicted by FIG. 1 showing a feed stream of crude TMA 12 passed into a fractionation column 10. In column 10, the feed is separated into a relatively low boiling point fraction which exits the top of the column through line 14 and a less volatile bottoms fraction which is removed from the base of the column through line 16. The distillate in line 14 is often referred to as overheads and comprises purified TMA which is condensed and recovered. The bottoms fraction is transferred to a reboiler 50 via line 16 where the bottoms are heated and returned to the fractionation column 10. The bottoms fraction comprises TMA and impurities including multivalent metals from the catalysts used to oxidize pseudocumene to form TMA. When the bottoms fraction is repeatedly recycled by the boiler 50 via lines 16 and 52, the concentration of impurities increases as well as the viscosity which often results in fouling. In order to reduce the viscosity of the bottoms and prevent fouling, artisans have resorted to maintaining large amounts of TMA as solvent in the bottoms fraction.

The specific teachings of TMA production may be found in the following U.S. Pat. Nos. all of which are hereby incorporated by reference: 4,754,062, 4,764,639, 4,786,753, 4,895,978, and 4,992,579.

Addition of Mineral Acid or Salt Thereof

The present invention is drawn towards adding a mineral acid or salt thereof to a TMA production process and/or a TMA distillation process for viscosity reduction. The mineral acid or salt thereof may be added at any point after the oxidation step of a TMA production process, such that it is present in the fractionation tower bottoms. Preferably the mineral acid or salt thereof is added after the crystallization and filtration step in order to prevent multivalent metal impurities from crystallizing as salts in the preparation of the trimellitic acid cake.

Examples of suitable mineral acids include sulfuric acid, nitric acid, boric acid, phosphoric acid, hydrobromic acid, and mixtures thereof. Suitable salts of these mineral acids include corresponding alkali or alkali earth salts. Phosphoric acid or an alkali or alkali earth metal thereof is preferred because: 1) it has a relatively low environmental impact, 2) it is not a strong oxidizing agent, and 3) it is inexpensive and may be added as an aqueous solution. Preferably, the phosphoric acid or alkali or alkali earth metal thereof is added to achieve a certain mole ratio of phosphorous to total multivalent metals present in the trimellitic acid cake produced by the crystallization and filtration step. This mole ratio of phosphorous to total multivalent metals is preferably from 1:10 to 10:1, more preferably from 1:4 to 4:1, and most preferably from 1:3 to 1:1.

EXAMPLES

Comparative Example

Trimellitic acid cake was obtained by: 1) oxidation of pseudocumene in the presence of a metal oxidation catalyst and an acetic acid solvent, 2) crystallization in a depressuring-cooling cycle with solvent removal, 3) separation of the crystals from the mother liquor by vacuum filtration, and 4) washing the crystals with acetic acid. The cake was then dropped into molten trimellitic anhydride for dehydration resulting in crude trimellitic anhydride. The crude trimellitic anhydride was then fed into a fractionation column for distillation. The TMA content and average residence time in the bottom of the fractionation tower was controlled by the amount of purging of this bottoms stream. This was adjusted to give about 80 weight percent TMA in the bottoms fraction in order to maintain the low viscosity needed for reliable operation (avoid fouling and plugging). The viscosity of the bottoms was measured using a Brookfield RVDV-II+ viscometer (available from Brookfield) with a S21 spindle at 100 rpm and at 400° F. and 450° F. Results for measurements at 400° F. may be found at column 1 of Table 1 below. Results for measurements at 450° F. may be found at column 1 of Table 2 below.

Example 1

Trimellitic acid cake was obtained by: 1) oxidation of pseudocumene in the presence of a metal oxidation catalyst and an acetic acid solvent, 2) crystallization in a depressuring-cooling cycle with solvent removal, 3) separation of the crystals from the mother liquor by vacuum filtration, and 4) washing the crystals with acetic acid. The amount of total multivalent metals impurities in the cake was determined by X-ray fluorescence. Phosphoric acid was then added to the cake in a 1:2 mole ratio of phosphorus to total multivalent metals. The cake was then dropped into molten trimellitic anhydride for dehydration resulting in crude trimellitic anhydride. The crude trimellitic anhydride was then fed into a fractionation column for distillation. The purge rate of the fractionation tower bottoms was adjusted to give a TMA content in the bottoms fraction of 80, 70, 65, and 60 wt % respectively, while the viscosity of the bottoms was monitored. The viscosity was measured using a Brookfield RVDV-II+ viscometer (available from Brookfield) with a S21 spindle at 100 rpm and at 400° F. and 450° F. Results for measurements at 400° F. may be found at column 2 of Table 1 below. Results for measurements at 450° F. may be found at column 2 of Table 2 below.

Example 2

Trimellitic acid cake was obtained by: 1) oxidation of pseudocumene in the presence of a metal oxidation catalyst and an acetic acid solvent, 2) crystallization in a depressuring-cooling cycle with solvent removal, 3) separation of the crystals from the mother liquor by vacuum filtration, and 4) washing the crystals with acetic acid. The amount of total multivalent metal impurities in the cake was determined by X-ray fluorescence. Phosphoric acid was then added to the cake in a 1:1 mole ratio of phosphorus to total multivalent metal. The cake was then dropped into molten trimellitic anhydride for dehydration resulting in crude trimellitic anhydride. The crude trimellitic anhydride was then fed into a fractionation column for distillation. The purge rate of the fractionation tower bottoms was controlled to maintain a low viscosity while reducing the TMA content in the bottoms fraction to 60 wt %. The viscosity of the bottoms was measured by a Brookfield RVDV-II+ viscometer (available from Brookfield) with a S21 spindle to measure the viscosity of the bottoms fraction at 100 rpm and at 400° F. and 450° F. Results for measurements at 400° F. may be found at column 3 of Table 1 below. Results for measurements at 450° F. may be found at column 3 of Table 2 below.

TABLE 1

(Viscosity Measured at 400° F.)*

| TMA wt. % in bottoms fraction | No $H_3PO_4$ Added | 1:2 Mole Ratio of $H_3PO_4$ to Metals | 1:1 Mole Ratio of $H_3PO_4$ to Metals |
|---|---|---|---|
| 80 | ~50 cps | ~50 cps | ** |
| 70 | ** | ~50 cps | ** |
| 65 | ** | ~80 cps | ** |
| 60 | ** | ~170 cps | 40 cps |

*viscosity was measured 2–5 times and averaged to the nearest ten
**no data

TABLE 2

(Viscosity Measured at 450° F.)*

| TMA wt. % in bottoms fraction | No $H_3PO_4$ Added | 1:2 Mole Ratio of $H_3PO_4$ to Metals | 1:1 Mole Ratio of $H_3PO_4$ to Metals |
|---|---|---|---|
| 80 | ~40 cps | ~40 cps | ** |
| 70 | ** | ~40 cps | ** |
| 65 | ** | ~40 cps | ** |
| 60 | ** | ~60 cps | ~20 cps |

*viscosity was measured 2–5 times and averaged to the nearest ten
**no data

As show by the tables above, the invention allows a drop of TMA wt. % from 80 to 60 without adversely affected viscosity. This represents an increase in yield of TMA recovered of 2%.

That which is claimed is:

1. A method for making trimellitic anhydride comprising:
   a) oxidizing pseudocumene in the presence of a solvent and a catalyst comprising multivalent metals to produce trimellitic acid;
   b) crystallizing and filtering said trimellitic acid to produce a crude trimellitic acid cake having impurities comprising said multivalent metals;
   c) dehydrating said crude trimellitic cake to form crude trimellitic anhydride; and
   d) distilling said crude trimellitic anhydride in a fractionation column to separate the crude trimellitic anhydride into a low boiling point fraction and a less volatile bottoms fraction;

wherein a viscosity reducer comprising an alkali or alkali earth metal salt of a mineral acid selected from the group consisting of sulfuric acid, nitric acid, boric acid, phosphoric acid hydrobromic acid, and mixtures thereof is added after step a) but before step d) so that said viscosity reducer is present in said bottoms fraction.

2. The method of claim 1 wherein the viscosity reducer is an alkali or alkali earth metal salt of a mineral acid chosen from the group consisting of sulfuric acid, nitric acid, boric acid, phosphoric acid hydrobromic acid, and mixtures thereof and is added to the crude trimellitic acid cake.

3. The method of claim 1 wherein the viscosity modifier is an alkali or alkali earth metal salt of phosphoric acid.

4. The method of claim 3 wherein the alkali or alkali earth metal salt of phosphoric acid is added to the crude trimellitic acid cake so that the mole ratio of phosphorus to total multivalent metals in said cake is from 1:10 to 10:1.

5. The method of claim 4 wherein said mole ratio is from 1:4 to 4:1.

6. The method of claim 4 wherein said mole ratio is from 1:3 to 1:1.

7. The method of claim 4 wherein said mole ratio is from 1:2 to 1:1.

8. A method for making trimellitic anhydride comprising:
   a) oxidizing pseudocumene in the presence of a solvent and a catalyst comprising multivalent metals to produce trimellitic acid;
   b) crystallizing and filtering said trimellitic acid to produce a crude trimellitic acid cake having impurities comprising said multivalent metals;
   c) dehydrating said crude trimellitic cake to form crude trimellitic anhydride; and
   d) distilling said crude trimellitic an hydride in a fractionation column, wherein a viscosity reducer, comprising phosphoric acid, is added to the crude trimellitic acid cake so that the mole ratio of phosphorus to total multivalent metals in said cake is 1:10 to 1:2.

9. The method of claim 8 wherein said mole ratio is from 1:4 to 1:2.

10. The method of claim 8 wherein said mole ratio is from 1:3 to 1:2.

* * * * *